United States Patent [19]

Knollenberg et al.

[11] 4,011,459
[45] Mar. 8, 1977

[54] METHOD AND APPARATUS FOR DETERMINING VALID SAMPLE VOLUME

[75] Inventors: Robert George Knollenberg; Robert E. Luehr, both of Boulder, Colo.

[73] Assignee: Particle Measuring Systems, Inc., Boulder, Colo.

[22] Filed: Dec. 5, 1975

[21] Appl. No.: 638,015

[52] U.S. Cl. .......................... 250/576; 73/432 PS; 250/208
[51] Int. Cl.[2] .................. G01N 21/26; H01J 39/12
[58] Field of Search ............... 73/432 PS; 250/208, 250/573, 561, 576; 324/71 CP

[56] References Cited

UNITED STATES PATENTS

| | | | |
|---|---|---|---|
| 2,494,441 | 1/1950 | Hillier | 324/71 CP |
| 2,839,963 | 6/1958 | Moss et al. | 250/573 |
| 3,941,479 | 3/1976 | Whitehead | 324/71 CP |

Primary Examiner—Harold A. Dixon
Attorney, Agent, or Firm—O'Rourke, Harris & Hill

[57] ABSTRACT

Method and apparatus for establishing a valid sample volume in a beam of radiation, wherein a sample stream is introduced substantially transversely to the radiation beam, an optical system is configured to produce images on first and second image planes, the two planes preferably being perpendicular to one another and established by means of a beam splitter, first and second photosensors being positioned in the image planes, the first photosensor having greater optical and an electronic gain and a masked portion, and the second photosensor being either unmasked or having masked portions corresponding generally to the unmasked portions of the first photosensor, the first photosensor being connected to comparator means and the second photosensor also being connected to the comparator means which accepts data only when the signal from second photosensor is of a greater magnitude than the signal from the first photosensor, whereby images on the photosensors from points outside the selected sample volume will be oriented with a sufficient portion of the image on the unmasked section of the first photosensor to produce a signal greater than that produced by the second photosensor thus rejecting data from that event.

15 Claims, 13 Drawing Figures

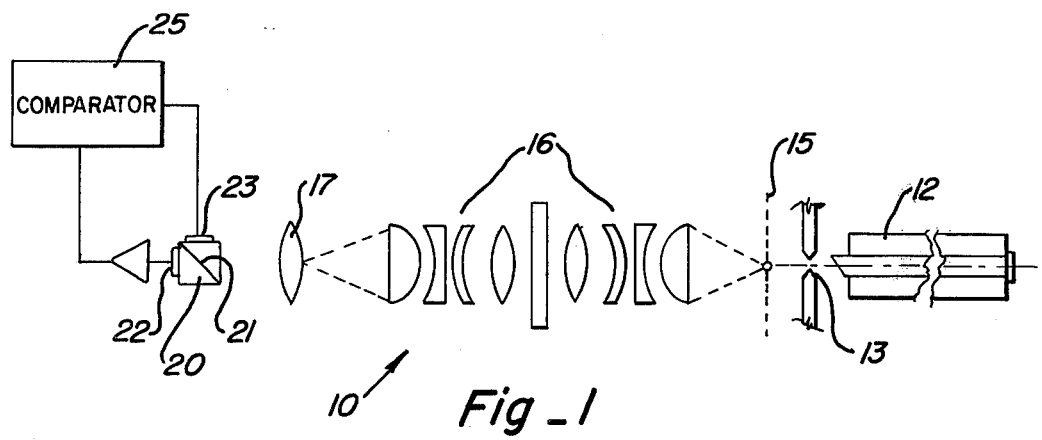
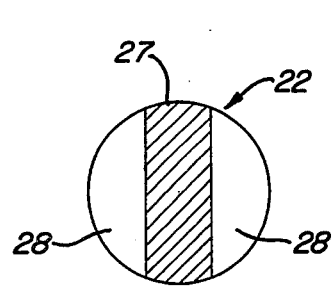
Fig_2
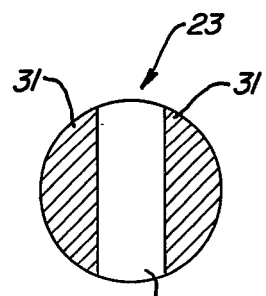
Fig_3
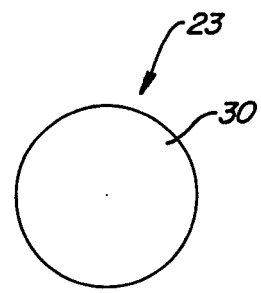
Fig_4
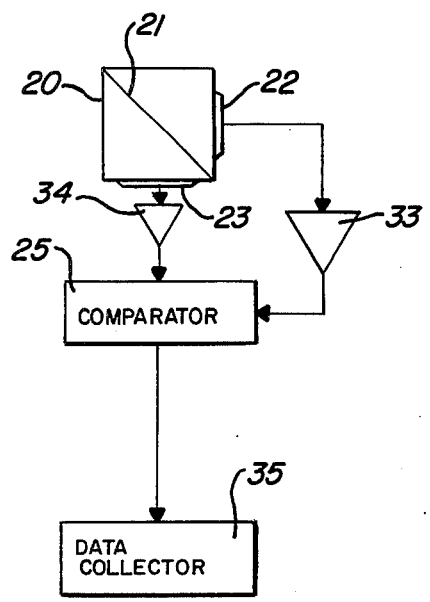
Fig_5
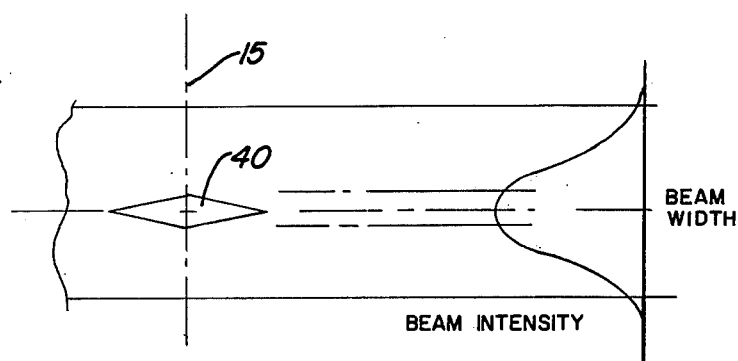
Fig_6

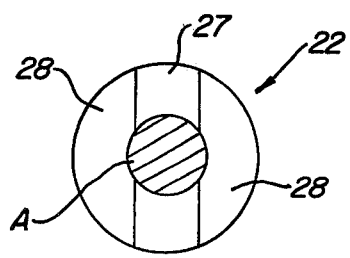
Fig_7
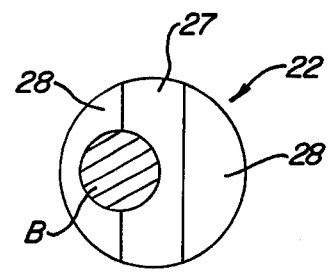
Fig_8
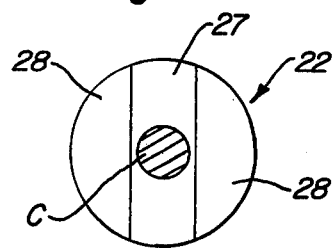
Fig_9
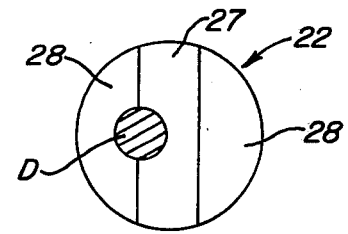
Fig_10
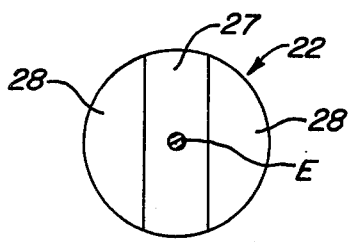
Fig_11
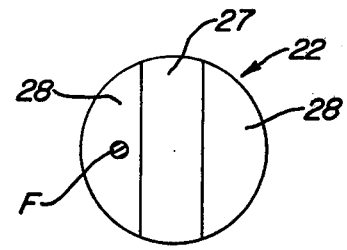
Fig_12
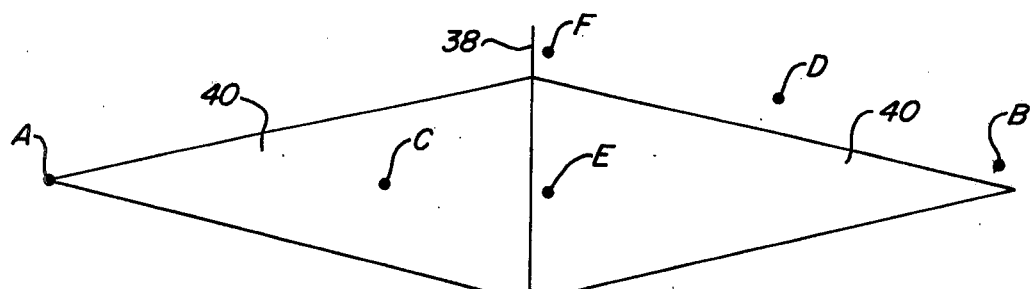
Fig_13

METHOD AND APPARATUS FOR DETERMINING VALID SAMPLE VOLUME

BACKGROUND OF THE INVENTION

1. Field of the Invention

The present invention relates generally to a method and apparatus for establishing a selected valid data volume preferably in the cross-sectional form of a diamond shape from which data is accepted. More specifically, the invention relates to a method and apparatus for illuminating particles suspended in a gas stream moving transversely through a radiation beam by generating two signals which are a function of the position of the particles and accepting only data for the particles producing preselected relative signal characteristics indicative of particle location in the desired volume.

2. Description of the Prior Art

Measurement of characteristics of particles suspended in a fluid stream, such as an air stream, by moving the fluid stream through a beam of radiation is known. However, spurious results are all too easily obtained unless the conditions of measurement are carefully controlled. For instance, a beam of coherent radiation varies substantially in intensity acorss the width thereof. Accordingly, if the brightness, transmission, backscatter, etc., of the beam with regard to an observed particle is a measured parameter, it is important that the measurement be made in a narrowly controlled portion of the beam. Similarly, the influence of a conduit directing a fluid stream through a beam of radiation is more significant adjacent the walls of the conduit. Accordingly, it is desirable that only a selected portion of the fluid stream be utilized for measurement.

Mechanical means can be utilized to limit the volumes from which data is accepted. With respect to particle measurement apparatus, a conduit can be employed to guide the particle only from the center of the beam. The disadvantage of this approach lies in the fact that such conduits themselves influence flow of particles, particularly when the particles are of substantial size relative to the beam, and, thus, introduce an uncertainty into the results.

Alternatively, the acceptability of data can be determined upon a statistical basis to discriminate against datum which, based upon certain measured parameters, is typical of events outside of the valid sample volume. However, such statistical approaches are relatively complicated and, not being a direct control, can exclude unusual but valid data.

SUMMARY OF THE INVENTION

The present invention, which provides a heretofore unavailable improvement over previous methods and apparatus for limiting and defining a selected volume from which data is acceptable, comprises utilization of an optical system, photosensors and electronic signal comparison to determine when an event is taking place within the preselected data volume — in which case the data is accepted — or outside of the preselected data volume — in which case the data is rejected. A magnifying optical system on the order of 10×, is positioned with the object plane at the center of the preselected valid sample volume. A beam splitter, preferably 50% but operably of other bias', is positioned to produce two image planes of the optical system. Each of the split beams falls upon a photosensor associated with the beam splitter and located in an image plane of the optical system. The first photosensor has a masked central area optimumally about ⅛ or more of the area of the photosensor, with the masked area being preferably bound by chords of the preferably round photosensor. The other photosensor is either unmasked or is masked in areas corresponding generally to the unmasked portions of the first photosensor. However, depending upon the desired sample volume, the masked areas may vary. An amplifier is provided in the circuit connection between the first photosensor and and electronic comparison means. The circuit connection to the second photosensor may include an amplifier provided the gain is ½ or less of the gain of the first photosensor, or the second photosensor may be directly connected to the electronic comparison means. An acceptable event is indicated when the signal from the first photosensor is less than that from the second photosensor.

Accordingly, an object of the present invention is to provide a new and improved device for defining a valid sample volume in a beam of radiation.

Another object of the present invention is to provide a new and improved method and apparatus for establishing a valid sample volume in a fluid stream through a beam of radiation.

Yet another object of the present invention is to provide a new and improved method and apparatus for limiting the depth of field from which data is accepted in a particle measuring device.

Still another object of the present invention is to provide a method and apparatus in which a valid sample volume may be conveniently altered.

These and other objects and features of the present invention will be apparent from the following description.

BRIEF DESCRIPTION OF THE DRAWINGS

In the drawings

FIG. 1 is a simplified view of an apparatus in accordance with the present invention;

FIG. 2 is a view of a photosensor in accordance with the present invention;

FIG. 3 is a view of a photosensor in accordance with an instant invention;

FIG. 4 is a view of an alternative sensor in accordance with the present invention;

FIG. 5 is a simplified schematic diagram of portion of the valid data acceptance device according to the instant invention;

FIG. 6 is an illustration of beam intensity as the abscissa and beam width as the ordinate of coherent radiation relative to a sample volume defined in accord with the instant invention;

FIGS. 7 through 12 are views of images of specific articles in various locations relative to the valid data volume in accordance with the instant invention; and, FIG. 13 is a sectional view of preselected volume in accordance with instant invention illustrating the specific location of the particles producing the images illustrated in FIGS. 7 through 12.

DETAILED DESCRIPTION OF THE INVENTION

With reference to the drawings, wherein like components are designated by like reference numerals throughout the various figures, a device for determining a valid sample volume in a particle measuring device is illustrated in FIG. 1 and generally designated by 10. More specifically, particle measuring device 10 comprises radiation source 12 arranged to project a beam of radiation, preferably coherent radiation, through aperture 13. Intersecting the beam is particle plane 15 which conducts a sample stream, i.e., particles to be measured suspended in a fluid such as air, through the beam of radiation. An imaging optical system 16, including object lense 17 is configured with the object plane thereof at particle plane 15.

Beam splitter 20, including the partial reflector mirror 21 located at an angle, preferably a 45° angle, to the radiation beam, is disposed such that first photosensor 22 and second photosensor 23 lie in the image plane of optical system 16 of each of the split portions of the radiation beam. Photosensors 22 and 23, which change electrical characteristics in response to radiation falling thereon either in respect to resistance, electrical potential or other such difference are connected to comparator 25 which determines the relative magnitude of the signals from photosensors 22 and 23.

As shown in FIG. 2, first photosensor 22 is provided with a masked area 27, which is not sensitive to radiation, as well as unmasked portion 28. Second photosensor 23 may be arranged with an opposite arrangement to that of photosensor 22 as in FIG. 3, i.e., with an unmasked center portion 30, which is sensitive to radiation, and masked side portions 31, which are not sensitive to radiation. Alternatively, shown in FIG. 4, the second photosensor 23 may be formed of completely unmasked portion 30. While photosensors 22 and 23 are shown as being of a circular configuration, this is only a preferred embodiment. The specific shape thereof the photosensors 22 and 23 do not constitute a critical aspect of the invention. Similarly, the specific shape of the masked areas are not critical since, as will be apparent to those skilled in the art, the masked areas are determined by the designated shape of the valid data volume.

The discrimination between valid and invalid data will be more readily understood with reference to FIG. 5. As shown in FIG. 5, the output from first photosensor 22 is increased by amplifier 33, which preferably has a gain of at least 2× relative to the output of second photosensor 23 through optional amplifier 34 but which may also have a variable gain. In the event that the signal from first photosensor 22 is greater than the signal of second photosensor 23, comparator 25 outputs a signal to data collector 35 indicating that the event is taking place in the preselected valid sample volume. This determination is made as a function of the displacement of the particle being measured from the particle plane 15.

The significance of the sample volume will be appreciated more fully with reference to FIG. 6. As shown, the Gaussian intensity profile for a laser beam varies substantially across the width of the beam. Thus data predicated upon the illumination of a particle in the beam can be merely a function of the particle position in the beam. However, by limiting measurement to sample volume 40 in the center position of the beam, data variations as a result of position in the beam width are almost entirely obviated.

With reference to FIG. 13, object A is substantially displaced from object plane 38 and is at the end of the preselected sample volume 40, which is shown as a diamond shaped area in section. Particle A produces an image on first photosensor 22 such as is shown in FIG. 7. The area of the image outside of masked area 27 is substantially equal to the area striking unmasked area 28. Accordingly, if second photosensor 23 is in the configuration shown in FIG. 4, and with the valid assumption that the signal generated by each of the photosensors is proportional to the area of the photosensor illuminated, the signal from first photosensor 22 as shown in FIG. 7 will be substantially equal to the signal from second photosensor 23 as shown in FIG. 4. Thus, in the ideal case, the information from particle A will be accepted. However, if another particle of the same size as particle A is positioned a bit further outside the selected sample volume 40, such as particle B in FIG. 13, the image on first photosensor 22 will be as shown in FIG. 8. In this instance, the image is clearly falling in a greater proportion upon the unmasked area 28 than on the masked area 27. Accordingly, the signal from first photosensor 22 will, after amplification as described above, substantially exceed that from second photosensor 23 as illustrated in FIG. 4.

Thus, the closer a particle is to the center of sample volumes 40, the more centrally aligned the image on the photosensors 22 and 23 will be. Also, the closer the particles are to object plane 38, the smaller the image on photosensors 22 and 23. Thus particle C shown in FIG. 13 as being substantially centered with a sample volume 40 and only modestly displaced from object plane 38 produces an image as shown in FIG. 9 almost entirely within the masked area 27 of first photosensor 22. Accordingly, the signal from first photosensor 22 will be essentially zero. However, particle D displaced from object plane 38 about the same distance as particle C but outside of the sample volume 40, will, as shown in FIG. 10, lie largely outside of masked area 27 and will produce a signal which, after amplification, will exceed that from second photosensor 23.

Particle E, being both near the center of sample volume 40 and adjacent object plane 38, clearly lies entirely within masked area 27 of first photosensor 22 as shown in FIG. 11. Thus the data associated with particle E would clearly be acceptable data. However, particle F, though adjacent object plane 38, lies entirely outside of sample volume 40, and, as shown in FIG. 12, would fall entirely in unmasked area 28 of first photosensor 22 and accordingly the amplified signal from first photosensor 22 would exceed that from second photosensor 23 indicating unacceptable data.

The above discussion has been primarily concerned with the signals from first photosensor 22, as shown in FIG. 2 relative to the signal from second photosensor 23 as shown in FIG. 4. However, second photosensor 23 may be in the configuration shown in FIG. 3 in which substantial portions are masked areas 31. Since the images on first and second photosensors 22 and 23 are of essentially the same size, intensity and orientation, it will be recognized that second photosensor 23 as shown in FIG. 3 will enhance the sensitivity of the apparatus since the signal from second photosensor 23 is shown in FIG. 3 will diminish as the image moves away from the preselected area corresponding substantially to masked area 27 of first photosensor 22.

The above referred embodiments have been illustrated with reference to, for instance, beam splitters of a 50–50 transmitted to reflected light ratio, fixed gain amplifiers, and other parameters indicating an ideal and constant testing situation. However, instead of employing amplifiers 33 and 34, the bias of transmitted to reflected light in beam splitter 20 could be such that the signals generated by first and second photosensors 22 and 23 are, without electrical amplification, of appropriate magnitude for comparison. Further, by selectively varying the gains of amplifiers 33 and 34, the effective depth of field may be varied since the percentage of the image falling outside of the masked area would then vary to provide the signal relationship necessary to activate comparator 35. Thus the instant invention also provides for convenient adjustment of the sample volume by utilizing a variable gain amplifiers 33 and 34.

Although only several embodiments of the present invention have been illustrated and described, it is anticipated that various changes and modifications will be apparent to those skilled in the art, and that such changes and modifications may be made within the scoepe of the following claims.

What is claimed is:

1. Apparatus for defining a valid sample volume comprising:
   means for providing a beam of radiation, imaging system means having an object plane and an image plane positioned to receive the beam of radiation, a beam splitter positioned between the object plane and the image plane to provide multiple image planes, a plurality of photosensors positioned one each in the image planes produced by the beam splitter with at least one of the photosensors being partially masked, comparator means connected to the outputs from the photosensors, and means for providing samples in the radiation beam, whereby samples within a predetermined defined sample volume are focused primarily on the masked section of the photosensor and produce a signal of less magnitude than that from the other photosensor thereby indicating acceptable data, and samples positioned outside of the predetermined sample volume fall primarily outside of the masked area and produce a signal greater than that from the other photosensor indicating invalid data.

2. Apparatus as set forth in claim 1 in which two photosensors are provided with the second photosensor being masked at least in part of the areas corresponding to the unmasked portion of the first photosensor.

3. Apparatus as set forth in claim 1 in which an amplifier is provided between the output of the masked photosensor and the comparator.

4. Apparatus as set forth in claim 3 in which the amplifier between the masked photosensor and comparator is a variable amplifier whereby the boundaries of the defined valid sample volume may be varied by varying the gain of the amplifier.

5. Apparatus as set forth in claim 1 in which the radiation produced by the means for providing a beam of radiation is coherent radiation.

6. Apparatus as set forth in claim 1 in which the means for providing a sample in the beam of radiation comprise means for providing a fluid stream perpendicular to the beam of radiation and substantially within the object plane to carry samples in the form of particles through the beam of radiation.

7. Apparatus as set forth in claim 6 in which the fluid stream is air.

8. Apparatus as set forth in claim 1 in which the beam splitter is biased to provide a greater percentage of radiation onto the masked photosensor than onto the other photosensor.

9. Apparatus for defining a valid sample volume comprising:
   a source of radiation in the form of a beam, an imaging optical system having an object plane and an image plane and positioned in the path of the beam of radiation, means for introducing a fluid stream having particles carried therein across the beam of radiation and at least partially within the obeject plane, a beam splitter positioned to intercept the beam of radiation and produce at least two image planes, a photosensor positioned in each image plane with one of the photosensors being partially masked with a fixed mask, and comparator means connected to the outputs from the photosensors with an amplifier between the connection from the partially masked photosensor and the comparator means.

10. Apparatus as set forth in claim 9 in which the photosensor sensors are of a round configuration and the partially masked photosensor is masked in an area bounded by parallel, equal length chords of the photosensor.

11. Apparatus as set forth in claim 9 in which there are two photosensors and the other photosensor is at least partially masked in areas corresponding to the unmasked areas of the first, partially masked photosensor.

12. Apparatus as set forth in claim 9 in which the optical system is a magnifying, imaging optical system.

13. A method for defining a valid sample in a beam of radiation comprising:
   generating a beam of radiation, passing a particle through the beam of radiation, producing an image of the particle by means of an optical system having an image plane and an object plane, passing the radiation through a beam splitter to produce at least two images, projecting an image on a first photosensor having a partially masked surface and generating a signal from the first photosensor as a result of the image formed thereon which is a function of the position of the particle relative to a predetermined volume in the beam of radiation, projecting a asecond image on a second photosensor and generating a signal from the second photosensor with the signal magnitude being a function of the radiation illuminating the particle, comparing the magnitudes of the two signals and accepting data generated with regard to the particle when the relative strengths of the signals as determined by the comparator indicate rhat the particle is within a preselected volume.

14. A method for defining a valid sample volume as set forth in claim 13 in which a stream of particles are passed through the beam of radiation in a perpendicular manner and entrained in an air stream.

15. A method for defining a valid sample volume as set forth in claim 13 in which the magnitude of the signal from athe second photosensor is also a function of the position of a particle relative to the predetermined volume.

* * * * *